United States Patent
Diehl

(10) Patent No.: US 6,254,765 B1
(45) Date of Patent: Jul. 3, 2001

(54) METHOD OF REGULATING THE TEMPERATURE OF A SENSOR

(75) Inventor: Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/382,756

(22) Filed: Aug. 25, 1999

(30) Foreign Application Priority Data

Aug. 25, 1998 (DE) .............................................. 198 38 456

(51) Int. Cl.$^7$ ................................................. G01N 27/409
(52) U.S. Cl. ......................... 205/785; 204/424; 219/497
(58) Field of Search .................................. 204/406, 408, 204/421–429; 205/784.5, 785; 73/23.25, 23.32; 219/202, 209, 490, 497; 123/697; 324/600, 601

(56) References Cited

U.S. PATENT DOCUMENTS

| | | | |
|---|---|---|---|
| 4,419,190 | * 12/1983 | Dietz et al. | 204/408 |
| 4,505,802 | * 3/1985 | Mase et al. | 204/425 |
| 5,461,902 | * 10/1995 | Iwata | 73/23.32 |

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

A method for regulating the temperature of a sensor for determining an oxygen concentration in gas mixtures, in particular in exhaust gases of internal combustion engines, where a detection voltage that corresponds to the oxygen concentration and is supplied by a Nernst measurement cell is analyzed, the sensor is adjusted to an operating temperature by a heating device, and the instantaneous operating temperature is determined from a measurement of an internal a.c. resistance of the Nernst measurement cell. In starting and/or restarting operation of the sensor, an internal a.c. resistance of a lead of electrodes of the Nernst measurement cell is determined, and the instantaneous internal a.c. resistance thus determined is taken into account in determining the operating temperature.

10 Claims, 2 Drawing Sheets

METHOD OF REGULATING THE TEMPERATURE OF A SENSOR

FIELD OF THE INVENTION

The present invention relates to a method of regulating the temperature of a sensor for determining an oxygen concentration in gas mixtures, in particular in exhaust gases of internal combustion engines.

BACKGROUND INFORMATION

Sensors are used to preset a fuel-air mixture for operation of an internal combustion engine by determining the oxygen concentration in the exhaust gas of the engine. The fuel-air mixture may be in the rich range, i.e., the fuel is present in stoichiometric excess, so that only a small amount of oxygen is present in the exhaust gas in comparison with other partially unburned components. In the lean range, where more oxygen than air is present in the fuel-air mixture, the oxygen concentration in the exhaust gas is high accordingly.

Lambda probes are known for determining the oxygen concentration in the exhaust gas, detecting a lambda value>1 in the lean range or <1 in the rich range and lambda=1 in the stoichiometric range. In a known way, a Nernst measurement cell of the sensor supplies a detection voltage which is sent to a circuit arrangement. The detection voltage is determined here by a difference in oxygen concentration at an electrode exposed to the gas for measurement and at an electrode of the Nernst measurement cell exposed to a reference gas. The detection voltage increases or decreases according to the oxygen concentration in the exhaust gas. A solid electrolyte body which is conductive for oxygen ions is arranged between the electrodes of the Nernst measurement cell.

Such sensors must be heated to temperatures above approximately 300° C. in the active range in order to achieve the necessary ion conductivity of the solid electrolyte. To achieve an increase in measurement accuracy of the sensor, it is known that the operating temperature of the sensor can be controlled and regulated as necessary. It is known, in addition, that a heating device may be provided for the sensor and can be turned on or off in accordance with an operating temperature measured by the sensor.

To determine the operating temperature, it is known that an alternating voltage can be applied to the Nernst measurement cell and an a.c. resistance of the sensor can be determined with a measurement device.

A disadvantage of the known method is that the temperature-dependent a.c. resistance is determined by starting with a constant a.c. resistance of the electrodes, the solid electrolyte and the leads to the electrodes. The leads here have approximately 50% of the total resistance of the Nernst measurement cell in the operating state. Due to a manufacturing scattering, the lead resistance is subject to a relatively great scattering, so the measurement device determining the a.c. resistance of the Nernst measurement cell has an error corresponding to this scattering. The measurement device adds this scattering error to a temperature-induced fluctuation in the a.c. resistance and supplies a corresponding faulty control signal for the heating device of the sensor. This regulates the sensor at an incorrect operating temperature.

SUMMARY OF THE INVENTION

The method according to the present invention has the advantage that the operating temperature of the sensor can be regulated accurately. Due to the fact that an internal a.c. resistance of a lead of electrodes of the Nernst measurement cell is determined in starting or restarting operation of the sensor, and the instantaneous internal resistance of the lead thus determined is taken into account in determinating the operating temperature, manufacturing fluctuations in the resistance value can be eliminated. The internal a.c. resistance of the Nernst measurement cell then measured during operation of the sensor in fact fluctuates only because of a change in temperature, so that the control signal supplied by the measurement device for the heating device can be supplied with a great accuracy. In particular, it is also advantageous that a change in resistance due to aging can be taken into account in resuming operation of the sensor due to the repeated measurement of the internal resistance of the lead.

In another preferred embodiment of the present invention, the instantaneous internal a.c. resistance of the lead is determined by a brief overheating phase of the heating device, while the total internal a.c. resistance is being measured. A constant value for the resistance component of the electrodes and the resistance component of the solid electrolyte between the electrodes is subtracted from this measured internal a.c. resistance. This yields the exact internal resistance of the lead of the sensor. Furthermore, it is preferable if a temperature coefficient of the electrodes is taken into account in the determination of the instantaneous internal resistance of the lead, so that the accuracy in determination of the actual internal resistance of the lead can be increased.

The method according to the present invention also offers the advantage that overheating of the sensor is prevented. Due to the fact that an internal a.c. resistance of a lead of the electrodes of the Nernst measurement cell is determined during operation of the sensor, in particular during a shutdown phase of the sensor, and the instantaneous internal a.c. resistance thus determined is taken into account in determining the operating temperature, fluctuations in the internal a.c. resistance can be taken into account to advantage during operation of the sensor. This makes it possible to turn the heating device of the sensor off and on in a controlled manner, preventing overheating of the sensor which could lead to heat stress cracks in the sensor. In particular since the internal resistance of the solid electrolyte body of the Nernst measurement cell is very small at the operating temperature of the sensor, fluctuations in the lead resistance to the Nernst measurement cell have strong effects accordingly.

DETAILED DESCRIPTION

Figure 1:
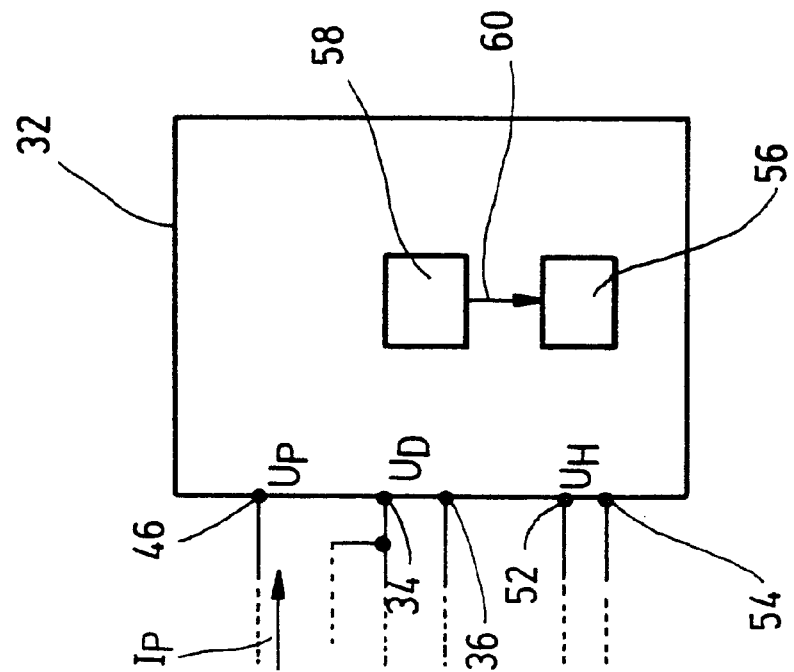
FIG. 1 shows a sectional diagram through a sensor.
Figure 1:
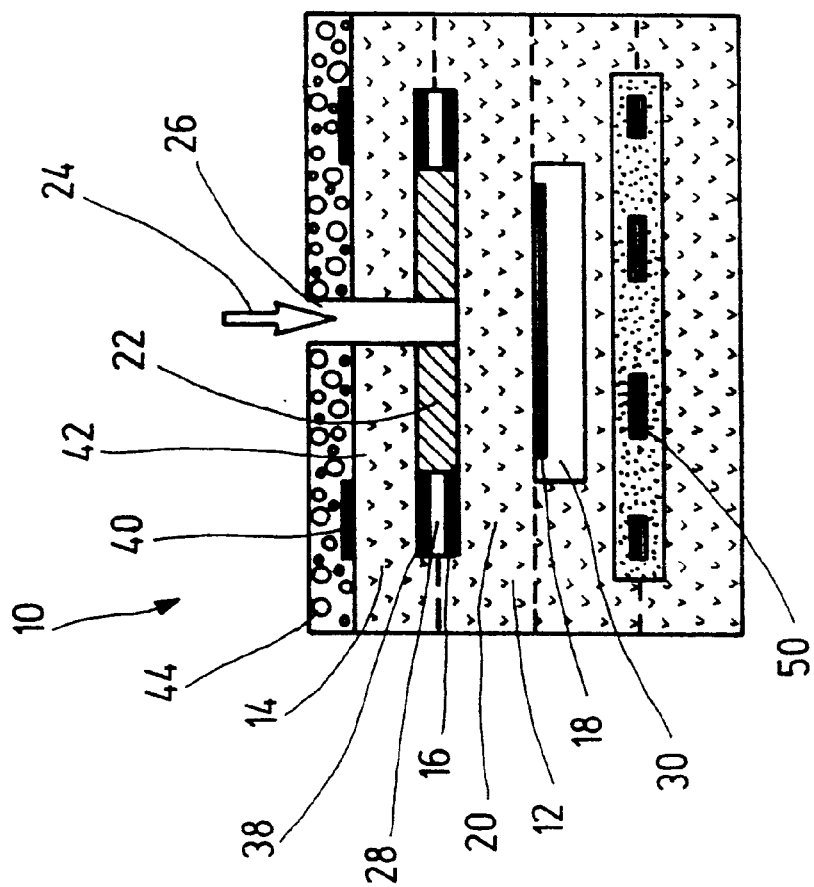

FIG. 1 shows a sensor 10 in a sectional diagram through a measurement head. Sensor 10 is designed as a planar broad-band sensor and is composed of a number of individual layers arranged one above the other, optionally structured, for example, by film casting, punching, screen printing, laminating, cutting, sintering or the like. Production of the layered structure will not be discussed in further detail in the present description because it is already known.

Sensor 10 is used to determine an oxygen concentration in the exhaust gases of internal combustion engines to obtain a control signal for setting a fuel-air mixture with which the internal combustion engine is operated. Sensor 10 has a Nernst measurement cell 12 and a pump cell 14. Nernst measurement cell 12 has a first electrode 16 and a second electrode 18 between which there is a solid electrolyte 20. Electrode 16 is exposed through a diffusion barrier 22 to exhaust gas 24 on which the measurement is to be performed. Sensor 10 has a measurement opening 26 which can receive exhaust gas 24. Diffusion barrier 22 extends at the base of measurement opening 26, forming a cavity 28 within which electrode 16 is arranged. Electrode 18 of Nernst measurement cell 12 is arranged in a reference air channel 30 and is exposed to a reference gas such as air in reference air channel 30. Solid electrolyte 20 is made of zirconium oxide stabilized with yttrium oxide, for example, while electrodes 16 and 18 are made of platinum and zirconium oxide, for example.

Sensor 10 is connected to a circuit arrangement 32, which is just indicated here and is used to analyze signals of sensor 10 and to control sensor 10. Electrodes 16 and 18 are connected here to inputs 34 and 36 to which a detection voltage $U_D$ of Nernst measurement cell 12 is applied.

Pump cell 14 has a first electrode 38 and a second electrode 40 between which there is a solid electrolyte 42. Solid electrolyte 42 is in turn composed of a zirconium oxide stabilized with yttrium oxide, for example, while electrodes 38 and 40 may be made of platinum and zirconium oxide. Electrode 38 is also arranged in cavity 28 and is thus also exposed to exhaust gas 24 through diffusion barrier 22. Electrode 40 is covered with a protective layer 44 which is porous, so that electrode 40 is exposed directly to exhaust gas 24. Electrode 40 is connected to one input 46 of circuit arrangement 32, while electrode 38 is connected to electrode 16 and is switched together with it to input 34 of circuit arrangement 32.

Sensor 10 also includes a heating device 50 formed by a heating wave form and connected to inputs 52 and 54 of circuit arrangement 32. A heating voltage $U_H$ can be applied to inputs 52 and 54 by a control circuit 56.

The function of sensor 10 is as follows.

Exhaust gas 24 enters cavity 28 through measurement opening 26 and diffusion barrier 22 and is thus applied to electrodes 16 of Nernst measurement cell 12 and electrode 38 of pump cell 14. Because of the oxygen concentration present in the exhaust gas on which the measurement is to be performed, an oxygen concentration difference is established between electrode 16 and electrode 18 exposed to the reference gas. Electrode 16 is connected by terminal 34 to a current source of circuit arrangement 32 which supplies a constant current. Because of a prevailing oxygen concentration difference at electrodes 16 and 18, a certain detection voltage (Nernst voltage) $U_D$ is established. Nernst measurement cell 12 operates here as a lambda probe which detects whether there is a high oxygen concentration or a low oxygen concentration in exhaust gas 24. It is clear on the basis of the oxygen concentration whether the fuel-air mixture with which the internal combustion engine is operated is a rich or lean mixture. Detection voltage $U_D$ drops or increases in changing from the rich range to the lean range or vice versa.

With the help of circuit arrangement 32, detection voltage $U_D$ is used to determine a pump voltage $U_P$ to be applied to pump cell 14 between its electrodes 38 and 40. Pump voltage $U_P$ is negative or positive, depending on whether detection voltage $U_D$ signals that the fuel-air mixture is in the rich or lean range, so that electrode 40 is switched either as a cathode or anode. Accordingly, a pump current $I_P$ which is established can be measured by a measurement device of circuit arrangement 32. With the help of pump current $I_P$ either oxygen ions are pumped from electrode 40 to electrode 38 or vice versa. Measured pump current $I_P$ is used to control a device for setting the fuel-air mixture with which the internal combustion engine is operated.

Heating voltage $U_H$ can be applied to outputs 54 and 52 of circuit arrangement 32 by control equipment 56, so that heating device 50 can be turned on and off. Sensor 10 can be brought to an operating temperature of more than approximately 300° C. by heating device 50. Sensor 10 is exposed to a certain varying thermal energy through exhaust gas 24 because of the fluctuations in speed of exhaust gas 24 and/or temperature fluctuations in exhaust gas 24. Heating device 50 must be turned on and off depending on the heating of sensor 10 by exhaust gas 24. To determine the instantaneous operating temperature of sensor 10, circuit arrangement 32 has a measuring circuit 58 by which an internal a.c. resistance of Nernst measurement cell 12 including its leads to circuit arrangement 32 can be measured. Internal a.c. resistance of Nernst measurement cell 12 is known to be temperature dependent, so that the operating temperature can be deduced from the measured internal a.c. resistance of Nernst measurement cell 12. Measuring circuit 58 supplies a signal 60 for heating control 56 depending on the measured operating temperature.

Figure 2:
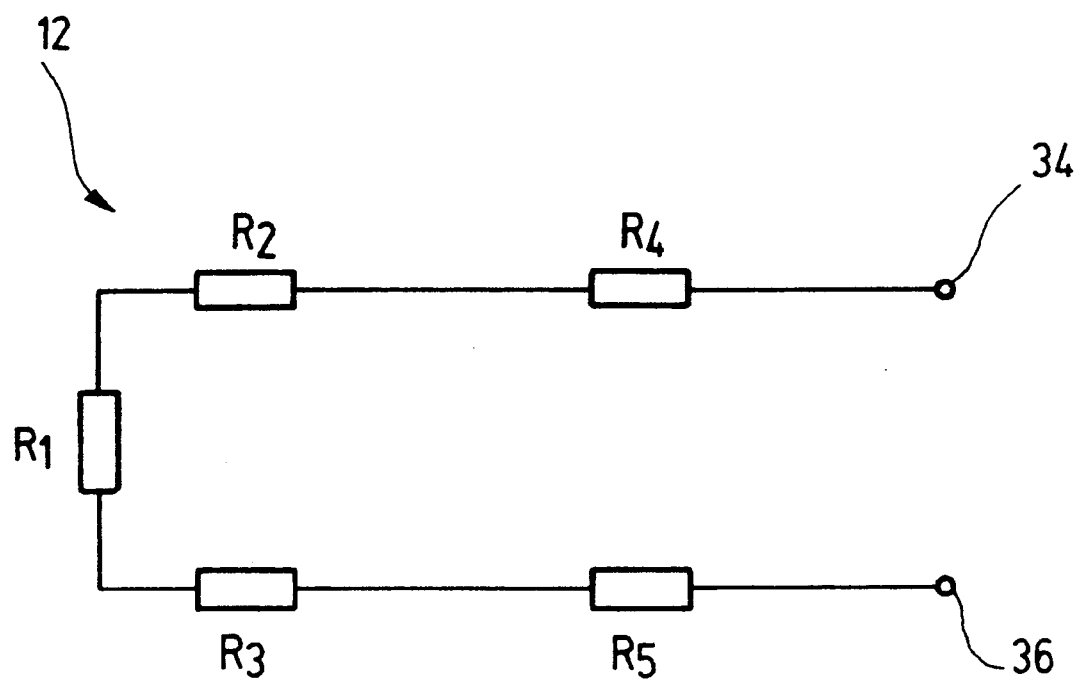
FIG. 2 shows an equivalent circuit diagram of a Nernst measurement cell of the sensor.

Determination of internal a.c. resistance of Nernst measurement cell 12 will be discussed in greater detail on the basis of the equivalent circuit diagram of Nernst measurement cell 12 shown in FIG. 2.

A total internal a.c. resistance $R_i$ of Nernst measurement cell 12 is composed of partial resistances $R_1$, $R_2$, $R_3$, $R_4$ and $R_5$. Resistance $R_1$ is obtained from the internal resistance of solid electrolyte body 20, resistance $R_2$ is obtained from the internal a.c. resistance of electrode 16, resistance $R_3$ is obtained from the internal a.c. resistance of electrode 18, resistance $R_4$ is obtained from the internal a.c. resistance of the lead of electrode 16 to terminal 34, and resistance $R_5$ is obtained from the internal a.c. resistance of the lead of electrode 18 to terminal 36.

Internal a.c. resistances $R_1$, $R_2$ and $R_3$ are known on the basis of the structural design of sensor 10. Resistances $R_4$ and $R_5$ depend on the structuring of the leads, which are usually formed by printed conductors applied by screen printing and are subject to manufacturing fluctuations. The value of the sum of resistances $R_1+R_2+R_3$ amounts to 10Ω, for example, at the operating temperature, while the value of the sum of resistances $R_4+R_5$ may be between 40Ω and 80Ω, for example. Thus, different internal a.c. resistances of Nernst measurement cell 12 of 50 to 90Ω, for example, may occur at sensors 10 with identical designs.

Sensor 10 is overheated briefly by heating device 50 when starting up or resuming operation of sensor 10. During this overheating phase, the a.c. resistance of Nernst measurement cell 12 is determined by measuring circuit 58. Then an a.c. voltage is applied to Nernst measurement cell 12 in a known manner and is superimposed on actual detection voltage $U_D$. Determination of an a.c. resistance is generally known, so that it need not be discussed in detail here as part of the present description.

The sum of the known resistances $R_1+R_2+R_3$ is subtracted from a.c. resistance $R_i$ determined by measuring circuit 58 during the brief heating of sensor 10, so that an instantaneous a.c. resistance $R_l=R_4+R_5$ of the leads of Nernst cell 12 can be determined. This is thus determined individually for sensor 10, with manufacturing fluctuations in lead resistances now being taken into account.

The total internal a.c. resistance of Nernst measurement cell 12 which is now known is thus derived from $R_i=R_1+$ $R_2+R_3+$ instantaneously measured $R_4+R_5$. In the subsequent stabilization of a.c. resistance $R_i$ of Nernst measurement cell 12 at 100Ω, for example, which is accomplished by turning heating device 50 on and off, the actual internal resistance of the leads can thus be taken into account. By eliminating the manufacturing tolerances in stabilization of the operating internal a.c. resistance of Nernst measurement cell 12, sensor 10 can be operated at a "correct" operating temperature.

Instantaneous lead resistance $R_4+R_5$ of Nernst measurement cell 12 can be determined, for example, in a definable interval, i.e., instantaneous internal resistance $R_4+R_5$ is not determined with each restart of sensor 10, usually on starting the motor vehicle, but instead only with every n-th restart, e.g., with every hundredth start. This prevents excessive aging of heating device 50 and sensor 10 due to repeated overheating to determine the actual internal a.c. resistance of the lead. Thus, it is possible on the whole in operation of sensor 10 to adjust control signal 60 of measuring device 58 to the actual internal a.c. resistance of Nernst measurement cell 12, eliminating manufacturing tolerances in lead resistance of Nernst measurement cell 12. Thus, heating device 50 is turned on and off by heating circuit 56 in accordance with this corrected signal 60 to regulate the operating temperature of sensor 10.

What is claimed is:

1. A method of regulating a temperature of a sensor for determining an oxygen concentration in an exhaust gas of an internal combustion engine, comprising the steps of:

detecting a detection voltage that corresponds to the oxygen concentration and that is supplied by a Nernst measurement cell that includes electrodes having leads;

adjusting the sensor to an operating, temperature by a heating device;

determining an instantaneous internal a.c. resistance of the leads of the electrodes of the Nernst measurement cell in at least one of a starting operation and a restarting operation of the sensor;

determining an instantaneous second operating temperature as a function of the determined instantaneous internal a.c. resistance of the leads; and regulating the temperature of the sensor as a function of the determined second operating temperature.

2. The method according to claim 1, wherein the internal a.c. resistance is determined at each starting operation and restarting operation.

3. The method according to claim 1, wherein the internal a.c. resistance is determined at every n-th restart operation, where n>=2.

4. The method according to claim 1, further comprising the step of heating the sensor to a temperature above an operating temperature of the sensor during the determination of the internal a.c. resistance.

5. The method according to claim 1, wherein the step of determining the instantaneous internal a.c. resistance of the leads on the electrodes includes the steps of:

determining a total internal a.c. resistance of the Nernst measurement cell; and subtracting a sum of predetermined internal a.c. resistances of the electrodes and a solid electrolyte from the total internal a.c. resistance.

6. The method according to claim 1, wherein the internal a.c. resistance is determined as a function of a temperature coefficient of a material of the electrodes.

7. The method according to claim 1, wherein the instantaneous operating temperature is determined as a further function of a measurement of a total internal a.c. resistance of the Nernst measurement cell.

8. The method of claim 1, wherein the step of determining the instantaneous internal a.c. resistance of the leads on the electrodes includes the step of:

determining the internal a.c. resistance of the leads on the electrodes separately from a total internal a.c. resistance of the Nernst measurement cell.

9. A method of regulating a temperature of a sensor for determining an oxygen concentration in an exhaust gas of an internal combustion engine, comprising the steps of:

detecting a detection voltage that corresponds to the oxygen concentration and that is supplied by a Nernst measurement cell that includes electrodes having leads;

adjusting the sensor to an operating temperature by a heating device;

determining an instantaneous internal a.c. resistance of the leads of the electrodes of the Nernst measurement cell during a shut-down phase of the sensor;

determining an instantaneous second operating temperature as a function of the determined instantaneous internal a.c. resistance of the leads; and regulating the temperature of the sensor as a function of the determined second operating temperature.

10. The method according to claim 9, wherein the instantaneous operating temperature is determined as a further function of a measurement of a total internal a.c. resistance of the Nernst measurement cell.

* * * * *